US00PP11974P2

(12) United States Plant Patent
Bradford

(10) Patent No.: US PP11,974 P2
(45) Date of Patent: Jul. 3, 2001

(54) PEACH TREE 'GOLDEN PRINCESS'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 09/472,604

(22) Filed: Dec. 27, 1999

(51) Int. Cl.[7] ..... A01H 5/00
(52) U.S. Cl. ..... Plt./197
(58) Field of Search ..... Plt./197

(56) References Cited

U.S. PATENT DOCUMENTS

P.P. 7,070 12/1989 Bradford et al. ..... Plt./197

*Primary Examiner*—Bruce R. Campell
*Assistant Examiner*—Wendy A Baker

(57) ABSTRACT

The present invention relates to a peach tree, *Prunus persica*, and more particularly to a new and distinct variety broadly characterized by a medium sized, vigorous, hardy, self-fertile, productive and regular bearing tree. The fruit matures under the ecological conditions described approximately the first week in August, with first picking on Aug. 7th, 1999. The fruit is uniformly large in size, very good in flavor, globose in shape, clingstone in type, firm in texture, yellow in flesh color, and mostly red in skin color. The variety was developed as a first generation cross using Crown Princess (U.S. Plant Pat. No. 7,070) yellow flesh peach as the selected seed parent and an unnamed white flesh nectarine as the selected pollen parent.

1 Drawing Sheet

BACKGROUND OF THE VARIETY

In a continuing effort to improve the quality of shipping fruits, I, the inventor, typically hybridize a large number of nectarine, peach, plum, apricot, and cherry seedlings each year. The present invention relates to a new and distinct variety of peach tree (*Prunus persica*), which has been denominated varietally as 'Golden Princess'. The present variety was hybridized by me in 1992, grown as a seedling on its own root in the greenhouse, and transplanted to a cultivated area of our experimental orchard at Bradford Farms near Le Grand, Calif. in Merced County (San Joaquin Valley). It was developed as a first generation cross using Crown Princess (U.S. Plant Pat. No. 7,070) yellow flesh peach as the selected seed parent and an unnamed white flesh nectarine as the selected pollen parent. Subsequent to origination of the present variety of peach tree, I asexually reproduced it by budding and grafting, in the experimental orchard described above, and such reproduction of plant and fruit characteristics were true to the original plant in all respects. The reproduction of the variety included the use of Nemaguard Rootstock (unpatented), the standard of the stone fruit industry in central California, upon which the present variety was compatible and true to type. The present variety is similar to its selected seed parent, Crown Princess (U.S. Plant Pat. No. 7,070) peach, by producing large clingstone peaches that are globose in shape, firm in texture, mostly red in skin color and yellow in flesh color, but is distinguished therefrom and an improvement thereon by having reniform instead of globose glands and by producing fruit that is subacidic instead of acidic in flavor and that ripens about sixty days later.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of peach tree, the following has been observed of a 5 year-old tree grown under the ecological conditions prevailing near Le Grand, Merced County (San Joaquin Valley), Calif., and was developed at the state of firm ripe on Aug. 9, 1999. However, during 1999 most stone fruit varieties in California ripened approximately ten days later than normal. All major color code designations are by reference to the Inter-Society Color Council, National Bureau of Standards. Common color names are also used occasionally.

TREE

Size: Medium, reaching and maintaining a height of 12' [3.66 meters] after 5 growing seasons utilizing typical dormant pruning.

Vigor: Vigorous, responding typically to irrigation and fertilization. The plant should be grown on a standard commercial rootstock for production purposes. The variety grows about 3' [0.91 meters] of surplus top-growth during the spring and summer.

Growth: Upright and dense.

Form: Vase formed.

Hardiness: Hardy with respect to central California winters.

Production: Productive, thinning necessary.

Bearing: Regular bearer with no alternate bearing yet observed.

Fertility: Self-fertile.

Trunk:

*Size.*—Medium, reaching a maximum diameter of 5.5" [140 mm.] after the seventh growing season.

*Texture.*—Rough.

*Bark color.*—Grayish brown [61. gy.Br].

*Lenticels.*—Numerous.

*Color.*—Deep orange yellow [69. deep OY].

*Size.*—5/16" to ½" [7.9–12.7 mm.].

Branches:
*Size.*—Medium, typical of *Prunus persica.*
*Color.*—1st Year Wood Topside: Light grayish red [18.1.gy.R]. 1st Year Wood Underside: Brilliant yellow green [116. brill.YG]. Older Wood: Moderate brown [58. m.Br].
*Texture.*—Smooth on 1st year wood, increasing roughness with age.
*Lenticels.*—Numerous. Color: Light yellowish brown [76. l.yBr]. Size: 1/32" to 1/8" [0.8–3.2 mm.].

Leaves:
*Size.*—Large. Average Length: 6¾" [172 mm.]. Average Width: 1⅞"[47.6 mm.].
*Thickness.*—Medium.
*Form.*—Elliptical.
*Apex.*—Acuminate.
*Base.*—Acute.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: 7/16" [11.1 mm.]. Average Thickness: 1/16" [1.6 mm.]. Color: Light yellow green [119. l.YG].
*Stipules.*—Numerous, 2 per leaf, up to 6 per growing tip. Average Length: ⅜" [9.5 mm.].
*Glands.*—Numbers: 1 to 6, but most often 2. Position: Alternately positioned on the petiole and the base of blade. Size: Medium. Form: Reniform. Color: Light yellow green [119. l.YG].

Flower buds:
*Hardiness.*—Hardy, with respect to central California winters.
*Diameter.*—Typically ⅜" [9.5 mm.] 1 week before bloom.
*Length.*—Typically ¾" [19.1 mm.] 1 week before bloom.
*Form.*—Not appressed.
*Color.*—Dark purplish pink [251. d. p. Pk.].
*Surface.*—Pubescent.
*Color.*—Moderate purplish red [258. m.pR].

Flowers: Perfect, complete, perigynous, usually a single pistil, typically thirty or more stamens, five sepals and petal locations alternately positioned.
*Type.*—Showy.
*Number of petals.*—Usually five, a few doubles.
*Number per cluster.*—Generally from 1 to 3.
*Petal shape.*—Rounded.
*Petal margin.*—Slightly wavy.
*Average petal diameter.*—¾" [19.1 mm.].
*Petal color.*—Light purplish pink [249. l.pPk].
*Anther color.*—Dark red [16. d.R] when first open.
*Average pistil length.*—¾" [19.1 mm.].
*Fragrance.*—Strong when nectar is present.
*Average flower diameter.*—1¾" [44.5 mm.].
*Blooming period.*—Somewhat late compared with other varieties.
*Onset of bloom.*—One percent on Mar. 9, 1999.
*Duration of bloom.*—One to two weeks, dependent on ambient temperature.

FRUIT

Maturity when described: Firm ripe, Aug. 9, 1999, noting the 1999 ripening season was delayed about 10 days later than normal in California.

Date of first picking: Aug. 7, 1999.
Date of last picking: Aug. 16, 1999.
Size: Uniform, large.
*Average diameter axially.*—2⅞" [73.0 mm].
*Average diameter across suture plane.*—3" [76.2 mm].
*Typical weight.*—7.76 ounces [220 grams].
Form: Uniform, symmetrical, globose.
*Longitudinal section form.*—Round.
*Transverse section through diameter.*—Round.
Suture: A sharp crease in the stem cavity transforming to a shallow groove along the lateral surface becoming deeper at the apex with a slight depression beyond the pistil point.
Ventral surface: Strongly rounded, slightly lipped throughout.
Lips: Slightly unequal.
Cavity: Flaring, elongated in the suture plane, suture showing on one side, deep stem markings typical.
Base: Rounded to truncate.
Apex: Rounded.
Pistil point: Very short, apical, usually depressed within the suture.
Stem: Medium.
*Average length.*—⅜" [9.5 mm.].
*Average width.*—3/16" [4.8 mm.].

Skin:
*Thickness.*—Medium.
*Texture.*—medium.
*Tenacity.*—Tenacious to flesh.
*Astrigency.*—Slight to none.
*Tendency to crack.*—None observed.
*Color.*—Dark red [16. d.R] over a moderate reddish orange [37. m.rO] background, moderate orange yellow [71. m.OY] stem markings typical on the base, and light yellowish brown [76. l.yBr] stitching denoting the suture.
*Surface of pit cavity.*—*Dark red* [16. d.R] fibers breaking when twisted away from the stone.

Down: Moderate, short, does not roll up when rubbed.
Flesh:
*Color.*—Brilliant orange yellow [67. brill.OY] with some dark red [16. d.R] streaking very close to the stone.
*Amygdalin.*—Scarce.
*Juice.*—Abundant, rich.
*Texture.*—Firm, crisp.
*Fibers.*—Abundant, fine, tender.
*Ripens.*—Earliest toward the apex.
*Flavor.*—Subacidic and sweet averaging 14 brix.
*Aroma.*—Slight.
*Eating quality.*—Very good.

STONE

Type: Clingstone.
Form: Oval.
Base: Straight.
Apex: Slightly acute with a sharp point individually protruding about 1/16" [1.6 mm.].
Sides: Equal.
Surface: Irregularly furrowed near the apex and pitted toward the base.
Ridges: Jagged toward the base.
Color: Moderate brown [58. m.Br].
Pit wall: ¼" [6.4 mm.] thick.
Tendency to split: Slight.

Kernel:

*Form.*—Oval.

*Color.*—Strong orange yellow [68. s.OY] with light brown [57. l.Br] veins when first exposed.

*Taste.*—Very bitter.

*Viable.*—Yes.

*Average width.*—7/16" [11.1 mm.].

*Average length.*—5/8" [15.9 mm.].

Pellicle color: Moderate brown [58. m.Br].

Amygdalin: Abundant.

USE

Market: Fresh and long distance shipping.

Keeping quality: Fruit quality observed to remain in good condition in excess of 17 days in standard cold room at 36° Fahrenheit [2° Celsius].

Resistance to insects: No unusual susceptibilities noted.

Resistance to diseases: No unusual susceptibilities noted.

Although the new variety of peach tree possesses the described characteristics under the ecological conditions to Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is similar to its selected seed parent, Crown Princess (U.S. Plant Pat. No. 7,070) peach, by producing large clingstone peaches that are globose in shape, firm in texture, mostly red in skin color and yellow in flesh color, but is distinguished therefrom and an improvement thereon by having reniform instead of globose glands and by producing fruit that is subacidic instead of acidic in flavor and that ripens about sixty days later.

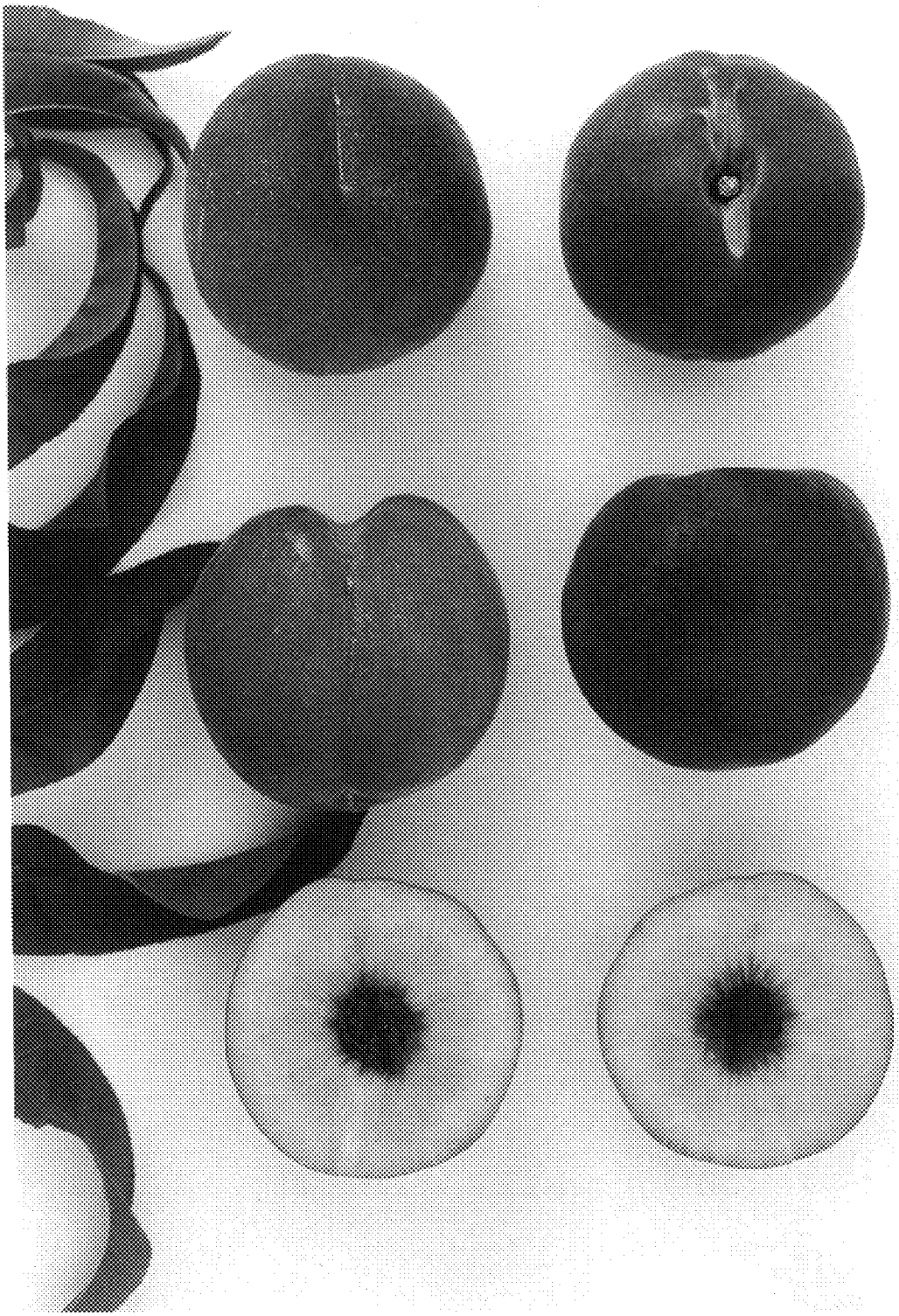

* * * * *